United States Patent [19]
Darsow et al.

[11] Patent Number: 6,037,504
[45] Date of Patent: Mar. 14, 2000

[54] PROCESS FOR PRODUCING ALIPHATIC DIOLS

[75] Inventors: Gerhard Darsow; Wolfgang Dummer; Wilfried Niemeier, all of Krefeld, Germany

[73] Assignee: Bayer Aktiengesellschaft, Leverkusen, Germany

[21] Appl. No.: 09/204,903

[22] Filed: Dec. 3, 1998

[30] Foreign Application Priority Data

Dec. 10, 1997 [DE] Germany .............................. 197 54 788

[51] Int. Cl.$^7$ ..................................................... C07C 29/14
[52] U.S. Cl. ............................................. 568/864; 568/852
[58] Field of Search ...................................... 568/864, 852

[56] References Cited

U.S. PATENT DOCUMENTS 5,696,303 12/1997 Darsow et al. .......................... 568/864

FOREIGN PATENT DOCUMENTS

| | | |
|---|---|---|
| 1023750 | 2/1958 | Germany . |
| 2321101 | 11/1974 | Germany . |
| 1300889 | 12/1972 | United Kingdom . |
| 1534232 | 11/1978 | United Kingdom . |
| 82/03854 | 11/1982 | WIPO . |

*Primary Examiner*—Paul J. Killos
*Attorney, Agent, or Firm*—Joseph C. Gil; Lyndanne M. Whalen; Diderico van Eyl

[57] ABSTRACT

In a process for producing aliphatic α,ω-diols comprising 4 to 12 C atoms from aliphatic α,ω-dicarboxylic acids comprising 4 to 12 C atoms, an oligoester of average chain length n=3 to n=4.5 and with an acid number of 40 to 60 mg KOH/g reaction mixture is first formed from a diol and a dicarboxylic acid, which oligoester is thereafter catalytically hydrogenated in the liquid phase. Hydrogenation is carried out continuously at 180 to 250° C. and at an $H_2$ pressure of 100 to 400 bar, over a pelletised catalyst which is free from Zn oxide and which comprises pressed powders of Cu, Mn and Al oxides with a content of at least one oxide of metals of subgroup VI of the periodic table of the elements (Mendeleev). The amount of $H_2$ is 20 to 100 times the amount required stoichiometrically.

14 Claims, No Drawings

PROCESS FOR PRODUCING ALIPHATIC DIOLS

The present invention relates to a simplified process for producing aliphatic α,ω-diols comprising 4 to 12 C atoms from aliphatic α,ω-dicarboxylic acids comprising 4 to 12 C atoms, in which only very small amounts are formed of the monoalcohols with C numbers of 1 to 12 which are usually formed as by-products on the hydrogenation of acids such as these or of ester derivatives thereof, and in which no $C_4$–$C_{12}$ lactones and no $C_4$–$C_{12}$ ω-hydroxycarboxylic acids are formed. For this purpose, the use of monoalcohols for ester production is avoided by firstly producing an oligomeric diol dicarboxylate from the carboxylic acid to be used and from the diol to be produced, which oligomeric diol carboxylate is of a defined average chain length (average ester length= degree of oligomerisation n=3 to n=4.5), which has an acid number of 40 to 60 mg KOH/g reaction mixture, and which is subsequently hydrogenated in the liquid phase with hydrogen, without further purification by distillation, over newly developed pelletised catalysts which are free from Zn oxide and which comprise pressed powders of Cu, Mn and Al oxides with a content of at least one oxide of metals of subgroup VI of the periodic table of the elements (Mendeleev), preferred Cr, Mo, W. Said conditions make the process environmentally and technically advantageous.

Aliphatic α,ω-diols, for example 1,6-hexanediol, are important monomers for the production of thermoplastic polyesters and of polyurethanes with special mechanical and chemical properties. For this purpose, diols such as these can be used in pure form or as a mixture of a plurality of diols of different chain lengths within the $C_4$–$C_{12}$ range.

For the production of 1,6-hexanediol, for example, it is known that adipic acid or salts thereof can be hydrogenated directly in aqueous solution or in an organic solvent, either batch-wise (DE-OS 26 05 107; GB 1,300,889) or continuously (DE-OS 23 21 101), wherein in addition to 1,6-hexanediol very large proportions of caprolactone, ω-hydroxy-caproic acid and monoalcohols with C numbers of 1 to 6 are always formed. Moreover, it is also known that adipic acid can be esterified for the same purpose with monoalcohols to form a di-n-alkyl adipate and that the latter can be hydrogenated in the gas phase to form 1,6-hexanediol (WO 82/03854). Furthermore, it is known that adipic acid can be esterified batch-wise with diols such as 1,6-hexanediol to form a mixture of higher esters with acid numbers of 10 to 15 mg KOH/g reaction product, and that these higher esters can be hydrogenated in a batch-wise autoclave process to form 1,6-hexanediol and esters of ω-hydroxy-caproic acid, wherein a copper chromite catalyst in powder form is used as the hydrogenation catalyst (DE-AS 10 23 750).

A process is known from EP-A 721 928 for producing aliphatic α,ω-diols comprising 4 to 12 C atoms from aliphatic α,ω-dicarboxylic acids comprising 4 to 12 C atoms by the oligoesterification of the dicarboxylic acids with the diols and catalytic hydrogenation of the resulting oligoester in the liquid phase. This process is characterised in that the oligoester is continuously hydrogenated over a pelletised catalyst consisting of pressed powders of Cu, Zn and Al oxides with or without a content of at least one oxide of metals of the iron group of the periodic table of the elements (Mendeleev) or of manganese, preferred Fe, Cr, Ni or Mn. This process is further characterised in that the oligoesterification has to be conducted batch-wise or quasi-continuously in 1 to 4 esterification steps, preferably quasi-continuously in 2 or 3 esterification steps, with removal of the water of reaction by distillation, and that the oligoester which is used has to be prepared so that a maximum acid number of 50 mg KOH/g oligoester (for oligomeric 1,6-hexanediol adipate this is a maximum of 32 mg KOH/g oligoester) is adhered to. Only apparatuses which comprise three esterification stages are described in the comparative examples. From a current viewpoint, a process such as this appears extremely laborious and costly.

It was therefore completely unexpected and surprising that when using the new catalysts, which are particularly suitable for the hydrogenation of oligoesters, these multi-stage esterification apparatuses are no longer necessary, because esterification can be effected, with permissible acid numbers of 40 to 60 mg KOH/g reaction mixture, within a short time in a single esterification stage. It has been possible to achieve this advance in processing because the new hydrogenation catalysts withstand considerably higher acid numbers of the oligoesters to be hydrogenated than was possible hitherto.

The present invention thus relates to a process for producing aliphatic α,ω-diols comprising 4 to 12 C atoms from aliphatic α,ω-dicarboxylic acids comprising 4 to 12 C atoms by the oligoesterification of said dicarboxylic acids with said diols in one reaction step and catalytic hydrogenation of the resulting oligoester in the liquid phase, which is characterised in that the oligoester is continuously hydrogenated at 180 to 250° C., preferably at 190 to 240° C., and at an $H_2$ pressure of 100 to 400 bar, preferably of 150 to 300 bar, wherein the amount of $H_2$ is 20 to 100 times the amount required stoichiometrically, over a pelletised catalyst which is free from Zn oxide and which consists of pressed powders of Cu, Mn and Al oxides with a content of at least one oxide of metals of subgroup VI of the periodic table of the elements (Mendeleev), preferred Cr, Mo, W.

The course of the reaction can be illustrated, with reference to the formation of 1,6-hexanediol from adipic acid using 1,6-hexanediol for the oligoesterification, by the following reaction scheme:

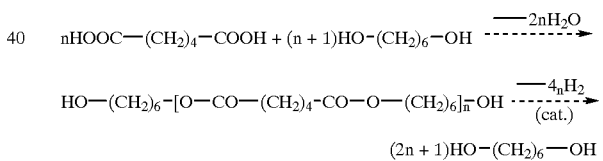

In the processes which have become known hitherto, very large amounts of by-products are frequently formed, which result in a considerable cost for the production of the reaction product in pure form. Recycling is not always possible, since, as stated above, hydrogenation to form the desired final product does not always proceed smoothly and would therefore result in a higher level of by-products being maintained in circulation. Another fundamental difficulty is due to the monoalcohol which has hitherto been used for esterification and which has to be separated from the final product. There is quite an obvious explanation for continued use of monoalcohols for esterification, namely that during the further development of the hydrogenation process from the liquid phase to the gaseous phase a readily volatilisable ester had to be available. The use of readily volatilisable esters of monoalcohols such as these is further supported by the fact that they can clearly be produced in pure form. This has appeared to be very important, since unpurified starting materials generally result in difficulties in hydrogenation processes. Esters such as these, which are formed from dicarboxylic acids and a lower alcohol, for example methanol, ethanol or propanol, generally necessitate the use of an esterification catalyst and of a water-entraining agent, such as toluene for example. Both of these constitute substances extraneous to the system which have to be separated. The use of a water-entraining agent, which has to be distilled off as an azeotropic mixture with the water of reaction from the reaction mixture, and which has to be separated from the water and recycled to the reaction mixture, means that the cost of the installation is increased. Moreover, a relatively large amount of energy has to be expended in order to distil the entraining agent, the amount of which is a multiple of the amount of water formed, from the reaction mixture again. Finally, the dicarboxylic acid dialkyl ester has to be carefully freed from esterification catalyst, by distillation or by other laborious purification measures, before catalytic hydrogenation is effected. After hydrogenation, the monoalcohol has to be separated from the reaction products, which is expensive to engineer, and has to be worked up to produce pure alcohol and recycled to the esterification process, whereupon losses of alcohol, which cannot be avoided, are increased.

If it is desired to esterify a dicarboxylic acid with higher boiling alcohols, for example those with C numbers >3, in order to hydrogenate them as dialkyl esters in the gas phase, the esterification catalyst and the entraining agent can possibly be dispensed with, but this again necessitates a substance which is extraneous to the reaction, namely the relatively expensive, higher boiling monoalcohol, which likewise has to be worked up again to produce pure alcohol and has to be recycled to the esterification process, whereupon losses of alcohol, which cannot be avoided, are also increased here. On account of the higher cost of alcohols such as these, this has an appreciable effect on the economic feasibility of a process such as this. Moreover, the cost of distillation is increased due to the higher boiling points involved.

The situation is different and more advantageous if a diol comprising 4 to 12 C atoms is used for the esterification of the dicarboxylic acid comprising 4 to 12 C atoms, since in a situation such as this neither esterification catalysts nor entraining agents are required, and since the esterification diol can remain in the reaction product as a substance which is intrinsic to the system. For the aforementioned purposes of use, it is permissible in many cases to employ a mixture of diols of different chain lengths; thus it is not necessary to use a diol with the same number of C atoms for the oligoesterification of the dicarboxylic acid. Rather, it is permissible according to the invention, for example, to react adipic acid not only with 1,6-hexanediol but also with 1,4-butanediol, 1,8-octanediol and other diols, in order to obtain a mixture of a $C_6$ diol with a $C_8$ diol for example. However, in order to obtain α,ω-diols with a uniform C number as reaction products, the dicarboxylic acid to be reacted is oligoesterified and hydrogenated with a diol of the same C number, for example adipic acid is oligoesterified and hydrogenated with 1,6-hexanediol, succinic acid is oligoesterified and hydrogenated with 1,4-butanediol, and suberic acid is oligoesterified and hydrogenated with 1,8-octanediol, etc.

Examples of dicarboxylic acids with an odd or even number of C atoms which can be used according to the invention, wherein the C atoms of the two carboxyl groups are always counted in conjunction, include succinic acid, glutaric acid, adipic acid, pimelic acid, suberic acid, heptanedicarboxylic acid, octanedicarboxylic acid and decanedicarboxylic acid. These are known and are obtainable from natural products and from synthetic sources.

α,ω-diols with an odd or even number of C atoms which are produced according to the invention and which can be used in the oligoesterification step include 1,4-butanediol, 1,5-pentanediol, 1,6-hexanediol, 1,7-heptanediol, 1,8-octanediol, 1,10-decanediol and 1,12-dodecanediol.

The process according to the invention is particularly important for the production of 1,6-hexanediol by the oligoesterification of adipic acid with 1,6-hexanediol and subsequent hydrogenation.

For the production of oligoesters such as those which are required in the process according to the invention, for example for the production of 1,6-hexanediol adipate, a batch process is normally employed in which the dicarboxylic acid and the diol are esterified in a reactor with or without a catalyst and the water formed during esterification is removed under reduced pressure, with or without an entraining agent, from the reaction mixture. Oligoesters such as these can be employed according to the invention so that the use of a plurality of reactors in series, such as those which are customarily employed in semi-continuous reaction cascades, is no longer necessary.

A suitable temperature range is the range from 100 to 240° C., and a suitable pressure range is that from 100 to 1500 mbar. On its own, however, conducting the process in one esterification step scarcely enables the relatively long times of reaction, of 12 hours or more for complete esterification for example, to be significantly shortened unless the removal of water from the reaction mixture is speeded up, for example by an installed high-speed stirrer system. It is possible to effect an additional speeding-up of the removal of water by blowing in an entraining gas, e.g. by blowing nitrogen in.

In this single-step procedure, however, the oligoesterification can also be conducted so that a plurality of reactors are filled with esterification mixture displaced in time with respect to each other over a defined chronological cycle. A new batch of oligoester is thus available for subsequent hydrogenation after a shorter time than that required for complete esterification.

Suitable reaction apparatuses for oligoesterification consist of acid-resistant material and are equipped with an effective stirrer and with a fitted distillation column of the usual type of construction comprising 8 to 15 plates.

For example, if a dicarboxylic acid is esterified with a diol in a molar ratio of 1:1 under the given esterification conditions, a mixture of oligoesters with different degrees of oligomerisation (=number of molecules of dicarboxylic acid in the oligoester) is obtained, the molecular weight distribution of which quite accurately follows a bell curve, the average degree of oligomerisation n of which in the sense of the above reaction scheme is n=7. The acid number is greater than 50 mg KOH/g reaction product. In order to shift the average chain length of the oligoester towards shorter chain lengths, it is advisable to conduct the esterification in the presence of a molar excess of diol. If the dicarboxylic acid is esterified with a diol in a molar ratio of 1:2 under the given reaction conditions, it is in fact certain that the free carboxyl groups will be esterified relatively rapidly and the mixture of oligoesters obtained will still only have an average chain length of n=5 for example, but a relatively large proportion of diol has to be used. It has now been found that oligoesters with an average chain length of 4 can be produced with the avoidance of longer times of reaction, even when there is only a slight excess of diol with respect to dicarboxylic acid and at acid numbers higher than 40 mg KOH/g reaction product. The molar ratio for the requisite oligoester is 1.0 to 1.15 moles, preferably 1.05 to 1.10 moles of diol per 1 mole of dicarboxylic acid. The average degree of esterification (degree of oligomerisation) which is thereby obtained falls within the range from n=3 to n=4.5, preferably n=4.

The dicarboxylic acids which are used and the diols which are used usually have a degree of purity of greater than 99%. Because substances extraneous to the system can be dispensed with within the scope of the process according to the invention, however, the purity of recycled distillation material from the hydrogenation step following oligoesterification is completely satisfactory, even if these recycled distillation materials contain small amounts of unhydrogenated oligoester. Recycled oligoesters such as these, and other constituents, have to be taken into consideration in order to determine said molar ratio of diol to dicarboxylic acid.

A further advantage of the process according to the invention is that the oligoesters which are produced in this manner can be further processed directly in the hydrogenation stage without additional purification steps.

The hydrogenation step in the process according to the invention is conducted in the liquid phase with excess hydrogen, the amount of which is at least 20 to 100 times that required stoichiometrically. Due to working in the liquid phase, there is a reduction in energy consumption compared with gas phase processes, which results in a cost saving.

Whereas a batch process is often still employed for the hydrogenation of esters, in which catalysts in powder form are used in suspension, the hydrogenation stage of the process according to the invention can be operated completely continuously. Moreover, the hydrogenation stage is carried out over a pelletised catalyst. The difficulties associated with catalysts in powder form are thereby circumvented, namely the difficulty of activating powder catalysts in a targeted and uniform manner, the difficulty of recirculating powder catalysts by means of special slurry pumps, and the difficulty of quantitatively separating powder catalysts from the reaction product. In particular, slurry pumps are subjected to high mechanical stresses. Furthermore, the quantitative removal of catalysts in powder form is costly, because this necessitates coarse and fine filtration using apparatuses of interchangeable design. Moreover, there is a considerable risk of the catalysts rapidly losing their activity due to these additional operations, and high consumptions of catalyst have to be accepted in addition. In contrast to the aforementioned difficulties, the new pelletised catalysts which are used according to the invention exhibit a high degree of insensitivity to acids and a high degree of insensitivity to pressure, and exhibit a high activity which is not impaired even over a period of one to several years. The last-mentioned advantage is very important, since frequent replacement of the catalyst is very costly, even for pelletised catalysts which are employed in a fixed bed.

The pelletised catalyst which is used according to the invention consists of pressed powders of Cu, Mn and Al oxides, the Cu content of which is 30.0 to 55.0% by weight, the Mn content of which is 3.0 to 15.0% by weight and the Al content of which is 10.0 to 25.0% by weight, calculated as the metal in each case, wherein all the above data is expressed with respect to the total amount of oxide powder mixture and the balance constitutes oxygen making up 100% by weight. A catalyst such as this can be used in this form for the hydrogenation stage according to the invention without further additions. However, it advantageously has an additional content of at least one oxide of metals of subgroup VI of the periodic table of the elements (Mendeleev), preferred Cr, Mo, W, and optionally contains a proportion of an alkaline earth compound, such as $Mg(OH)_2$ or MgO, $Ca(OH)_2$ or CaO, $Sr(OH)_2$ or SrO, or $Ba(OH)_2$ or BaO, with an alkaline earth metal content of 0.5 to 7.0% by weight, calculated as the metal and expressed with respect to the total weight of catalyst.

Suitable elements of subgroup VI are chromium, molybdenum and tungsten. Oxides of the elements chromium, molybdenum and tungsten, preferably chromium and molybdenum, can be used either individually or in a mixture of oxides of a plurality of said elements. The total amount of oxides of subgroup VI of the periodic table in the pressed oxide powder is 0.05 to 3.0% by weight, preferably 0.1 to 0.8% by weight, calculated as the metal and expressed with respect to the amount of the total oxide powder for the hydrogenation catalysts. If a plurality of oxides of elements of subgroup VI of the periodic table is used, each of these mixed oxides is present in an amount which is not less than 20% and not greater than 80% of said overall range of 0.05 to 3.0% by weight.

The support-free pelletised catalysts can be produced by customary methods by the press-compaction of the metal oxide powders under high pressure, in tabletting or pelletising machines for example, wherein graphite and/or adhesives can also be used in amounts of 0.5 to 3.0% by weight with respect to the total weight of the constituents to be pressed, in order to improve the bonding capacity of the metal oxide particles. Examples of the pelletised form of the catalysts include tablets, spheres or granules with dimensions of 2 to 10 mm, preferably 3 to 7 mm. In addition, shaped bodies in tablet form can be provided with an axial through-hole in order to increase their external surface area. On a macroscopic scale, shaped bodies such as these have a smooth surface. In order to achieve a high stability (service life) the pelletised catalysts must have a crushing strength of 50 to 200 N, preferably 70 to 170 N, as measured on the surface of the shaped bodies. Moreover, the pelletised catalysts have an internal specific surface of 10 to 90 $m^2/g$, preferably 30 to 80 $m^2/g$. The crushing strength of the support-free pelletised catalysts can be determined according to DIN 50 106. The determination of the internal specific surface is effected according to Analyt. Chem. 30 (1958), 1387, or according to Adsorption, Surface Area and Porosity, London 1967, Sections 2 and 6.

The shaped bodies which are used as hydrogenation catalysts, and which comprise pressed powders of Cu, Mn and Al oxides with a content of at least one oxide of metals of subgroup VI of the periodic table, have to be carefully reduced before use. This is effected by treatment with hydrogen at 180 to 280° C., wherein a mixture of 10 to 15% by volume of $H_2$ and 90 to 85% by volume of an inert gas (e.g. nitrogen) is used at the start of the treatment and the proportion of inert gas is reduced to zero % by volume in the course of the treatment. A treatment such as this is carried out over a period of about 12 to 24 hours and is terminated when the catalyst no longer consumes hydrogen, and consequently when no more water of reaction is formed.

The hydrogenation step in the process according to the invention is preferably conducted continuously in the liquid phase at 180 to 250° C., preferably at 190 to 240° C. and under an $H_2$ pressure of 100 to 400 bar, preferably 150 to 300 bar, using pure hydrogen.

Whereas it is possible in principle to cause the mixture of oligoesters which is to be hydrogenated to flow from top to bottom or from bottom to top in the hydrogenation reactor, it has proved to be advantageous to cause the mixture of oligoesters to flow over the catalyst from top to bottom (trickling phase). In the course of this procedure, the mixture of oligoesters to be hydrogenated can either flow over the catalyst together with the hydrogen which is introduced separately or which is admixed previously (co-current process), or can be made to flow in the opposite direction to the hydrogen (counter-current process).

The hydrogenation reactor can either be a single high-pressure tube made of steel or a steel alloy which is completely or partly filled with the catalyst, wherein for very large tube diameters it may be useful to employ the pelletised, support-free catalyst on racks (wire baskets or similar). High-pressure tube bundles inside a common shell can also be used, wherein the individual tubes are again completely or partly filled with the support-free pelletised catalyst.

The hourly catalyst loading can be 200 to 600 ml of oligoester mixture per liter of catalyst. Under said reaction conditions, high catalyst service lifetimes of 8000 to 16,000 hours can be achieved. After depressurisation, during which the excess hydrogen is recovered and can be reused after compression and after replacing the hydrogen consumed, the reaction mixture leaving the hydrogenation reactor consists of 97.5% by weight or more of the anticipated diol or of the anticipated mixture of diols. It contains a maximum of 2.0% by weight of low-boiling organic compounds and contains a maximum of 1.5% by weight of high-boiling compounds as a residue of higher molecular weight. The high-boiling compounds essentially constitute an unreacted mixture of oligoesters and can be recycled to the process, so that the overall selectivity of the process with respect to diols is at least 98.0% by weight. After the removal of the low-boiling and high-boiling fractions by distillation, the diol produced is obtained in a purity of at least 99.9% by weight and can be used in this purity for all further processing operations.

EXAMPLES

Example 1

A solution of 730.7 g (5 moles) adipic acid in 620 g (5.25 moles) 1,6-hexanediol was introduced at 100° C. into a reaction apparatus made of acid-resistant material with a volume of 5 liters, which was fitted with a high-speed stirrer system of the usual type (turbine agitator; speed of rotation 800 to 1200 rpm) and a distillation column (10 theoretical plates). The mixture was rapidly heated, with stirring, to a reaction temperature of 140 to 170° C. and the water of reaction formed was distilled off at normal pressure. The remainder of the water of reaction was finally removed after a residence time of 1.5 hours at a pressure of 400 mbar and at a reaction temperature of 170 to 190° C. The desired degree of esterification was achieved after a further residence time of 2.0 hours (3.5 hours in total). The oligomeric 1,6-hexanediol adipate (1265 g) which was obtained had an average degree of oligoesterification (=number of molecules of adipic acid in the oligoester) of n=4 (as measured by gel permeation chromatography) and an acid number of 50 mg KOH/g reaction mixture.

Example 2

A vertical, thermally insulated high-pressure tube made of stainless, acid-resistant metal, with an inside diameter of 45 mm and a length of 1 m, which had previously been flushed with nitrogen until it was free from oxygen, was filled with 1.4 liters of a hydrogenation catalyst which had been prepared by forming tablets from powders of copper, manganese, aluminium and chromium oxides. The copper content of the tablets was 41% by weight, the manganese content was 6.6% by weight, the aluminium content was 19.0% by weight and the chromium content was 0.46% by weight. At a cylinder height of 3 mm and a diameter of 3 mm, the tablets had a crushing strength of 100 N on the curved surface of the cylinder and had an internal specific surface of 45 m$^2$/g. In order to activate the catalyst, which contained a mixture of metal oxides, the tablets were first dried for 6 hours in the flow of nitrogen (max. temperature: 200° C., flow rate: 5 Nm$^3$ N$_2$/hour). The actual activation was effected at a nitrogen pressure of 200 bar and at a temperature between 180 and 280° C., wherein hydrogen was gradually admixed with the inert gas. The admixed proportion of hydrogen was not allowed to exceed 10 to 15% by volume in the initial phase. The nitrogen content of the gas mixture was progressively reduced over 24 hours, until pure hydrogen finally flowed through the reactor. The reaction was terminated when water of reaction, which was collected in a downstream trap, was no longer formed. After activation of the hydrogenation catalyst, the hydrogen pressure in the reactor system was increased to 300 bar. 300 g per hour of 1,6-hexanediol adipate as in Example 1, together with 5 Nm$^3$ hydrogen at a pressure of 300 bar, were subsequently pumped through the high-pressure tube, the 1,6-hexanediol-adipate being heated to a temperature of 230° C. in an upstream, electrically heated heat exchanger before it entered the high-pressure tube. The reaction product leaving the reaction tube (crude 1,6-hexanediol) was cooled to a temperature <60° C. in a second heat exchanger (water condenser) at 300 bar hydrogen pressure and was separated in a gas separator from excess hydrogen, which was recycled to the hydrogenation system. After further cooling to a temperature <30° C. and depressurisation to normal pressure, the reaction product was investigated by gas chromatography. It only contained 1.8% by weight of monoalcohols with C numbers of 1 to 6 as the low boiling fraction, and only contained 1.1% by weight of unreacted 1,6-hexanediol adipate as the high boiling fraction, so that the 1,6-hexanediol content of the organic reaction product was 97.1% by weight. After the removal of the low- and high-boiling fractions by distillation, the 1,6-hexanediol produced was obtained in a purity of ≧99.9% by weight. Since the higher-boiling fractions could be recycled to the process, the overall selectivity of the process with respect to 1,6-hexanediol was 98.2% by weight. After a run time of 3000 hours, the efficacy of the catalyst was unchanged, so that the composition of the reaction product did not vary over this length of time.

Example 3

A high-pressure tube as in Example 2 was filled under inert gas with 1.4 liters of a hydrogenation catalyst prepared by forming tablets from powders of copper, manganese, aluminium, chromium and molybdenum oxides. The copper content of the tablets was 42.0% by weight, the manganese content was 7.0% by weight, the aluminium content was 18.5% by weight, the chromium content was 0.48% by weight and the molybdenum content was 0.46% by weight. At a cylinder height of 5 mm and a diameter of 5 mm the tablets had a crushing strength of 105 N on the curved surface of the cylinder, and had an internal specific surface of 48 m$^2$/g. After activation of the hydrogenation catalyst as in Example 2, the hydrogen pressure was increased to 300 bar. 450 g per hour of 1,6-hexanediol adipate as in Example 1, together with 5 Nm$^3$ hydrogen at a pressure of 300 bar, were subsequently pumped continuously through the high-pressure tube, the 1,6-hexanediol-adipate being heated to a temperature of 225° C. before it entered the high-pressure tube. After the separation of excess hydrogen and cooling to a temperature <30° C., the reaction product (crude 1,6-hexanediol) was analysed by gas chromatography and contained 0.9% by weight of monoalcohols with C numbers of 1 to 6 as low-boiling fractions, and contained 0.8% by weight of unreacted 1,6-hexanediol adipate as the high boiling-fraction, so that the 1,6-hexanediol content was 98.3% by weight. After the removal of the low- and high-boiling fractions by distillation, the 1,6-hexanediol produced was obtained in a purity of 99.9% by weight. Since the higher-boiling fractions could be recycled to the process, the overall selectivity of the process with respect to 1,6-hexanediol was 99.1% by weight. After a run time of 3500 hours, the efficacy of the catalyst was unchanged, so that the composition of the reaction product did not vary over this length of time.

Example 4

A high-pressure tube as in Example 2 was filled under inert gas with 1.4 liters of a hydrogenation catalyst prepared by forming tablets from powders of copper, manganese, aluminium, chromium and tungsten oxides. The copper content of the tablets was 42.0% by weight, the manganese content was 7.0% by weight, the aluminium content was 18.5% by weight, the chromium content was 0.48% by weight and the tungsten content was 0.44% by weight. At a cylinder height of 5 mm and a diameter of 5 mm the tablets had a crushing strength of 102 N on the curved surface of the cylinder, and had an internal specific surface of 52 m$^2$/g. After activation of the hydrogenation catalyst as in Example 2, the hydrogen pressure was increased to 300 bar. 250 g per hour of 1,6-hexanediol adipate as in Example 1, together with 5 Nm$^3$ hydrogen at a pressure of 300 bar, were subsequently pumped continuously through the high-pressure tube, the 1,6-hexanediol-adipate being heated to a temperature of 225° C. before it entered the high-pressure tube. After the separation of excess hydrogen and cooling to a temperature <30° C., the reaction product (crude 1,6-hexanediol) was analysed by gas chromatography and contained 0.9% by weight of monoalcohols with C numbers of 1 to 6 as low-boiling fractions, and contained 1.8% by weight of unreacted 1,6-hexanediol adipate as a high-boiling fraction, so that the 1,6-hexanediol produced was obtained in a purity of 97.3% by weight. After the removal of the low- and high-boiling fractions by distillation, the 1,6-haxanediol produced was obtained in a purity of 99.9% by weight. Since the higher-boiling fractions could be recycled to the process, the overall selectivity of the process with respect to 1,6-hexanediol was 99.1% by weight. After a run time of 700 hours, the efficacy of the catalyst was unchanged, so that the composition of the reaction product did not vary over this length of time.

Example 5

A solution of 590.5 g (5 moles) succinic acid in 602 g (5.1 moles) 1,4-butanediol was introduced at 100° C. into a reaction apparatus made of acid-resistant material with a volume of 5 liters, which was fitted with a high-speed stirrer system of the usual type (turbine agitator; speed of rotation 800 to 1200 rpm) and a distillation column (10 theoretical plates). The mixture was rapidly heated, with stirring, to a reaction temperature of 120 to 130° C. and the water of reaction formed was distilled off at normal pressure. The remainder of the water of reaction was finally removed after a residence time of 1.5 hours at a pressure of 400 mbar and at a reaction temperature of 130 to 160° C. The desired degree of esterification was achieved after a further residence time of 2.0 hours (3.5 hours in total). The oligomeric 1,4-butanediol succinate (1095 g) which was obtained had an average degree of oligoesterification (=number of molecules of succinic acid in the oligoester) of n=4 (as measured by gel permeation chromatography) and an acid number of 58 mg KOH/g reaction mixture.

Example 6

A vertical, thermally insulated high-pressure tube made of stainless, acid-resistant metal, with an inside diameter of 45 mm and a length of 1 m, which had previously been flushed with nitrogen until it was free from oxygen, was filled with 1.4 liters of a hydrogenation catalyst which had been prepared by forming tablets from powders of copper, manganese, aluminium and chromium oxides. The copper content of the tablets was 41% by weight, the manganese content was 6.6% by weight, the aluminium content was 19.0% by weight and the chromium content was 0.46% by weight. At a cylinder height of 3 mm and a diameter of 3 mm, the tablets had a crushing strength of 100 N on the curved surface of the cylinder and had an internal specific surface of 45 m$^2$/g. In order to activate the catalyst, which contained a mixture of metal oxides, the tablets were first dried for 6 hours in the flow of nitrogen (max. temperature: 200° C., flow rate: 5 Nm$^3$ N$_2$/hour). The actual activation was effected at a nitrogen pressure of 200 bar and at a temperature between 180 and 280° C., wherein hydrogen was gradually admixed with the inert gas. The admixed proportion of hydrogen was not allowed to exceed 10 to 15% by volume in the initial phase. The nitrogen content of the gas mixture was progressively reduced over 24 hours, until pure hydrogen finally flowed through the reactor. The reaction was terminated when water of reaction, which was collected in a downstream trap, was no longer formed. After activation of the hydrogenation catalyst, the hydrogen pressure in the reactor system was increased to 300 bar. 350 g per hour of 1,4-butanediol succinate as in Example 5, together with 5 Nm$^3$ hydrogen at a pressure of 300 bar, were subsequently pumped through the high-pressure tube, the 1,4-butanediol succinate being heated to a temperature of 230° C. in an upstream, electrically heated heat exchanger before it entered the high-pressure tube. The reaction product (crude 1,4-butanediol) was cooled to a temperature <60° C. at 300 bar hydrogen pressure in a second heat exchanger (water condenser) and was separated in a gas separator from excess hydrogen, which was recycled to the hydrogenation system. After further cooling to a temperature <30° C. and depressurisation to normal pressure, the reaction product was investigated by gas chromatography. It only contained 1.0% by weight of tetrahydrofuran and 0.9% by weight of monoalcohols with C numbers of 1 to 4 as the organic low-boiling fractions, and only contained 1.1% by weight of unreacted 1,4-butanediol succinate as the high-boiling fraction, so that the 1,4-butanediol content of the organic reaction product was 97.0% by weight. After the removal of the low- and high-boiling fractions by distillation, the 1,4-butanediol produced was obtained in a purity of ≧99.9% by weight. Since the higher boiling fractions could be recycled to the process, the overall selectivity of the process with respect to 1,4-butanediol was 98.1% by weight.

We claim:

1. A process for producing an aliphatic α,ω-diol having 4 to 12 C atoms from an aliphatic α,ω-dicarboxylic acid having 4 to 12 C atoms by the oligoesterification of the dicarboxylic acid with the diol to form a diol carboxylate having an average chain length of n=3 to n=4.5 and an acid number of 40 to 60 mg KOH/g reaction mixture, and catalytic hydrogenation of the resulting oligoester in the liquid phase, characterized in that the oligoester is continuously hydrogenated at 180 to 250° C. and at an H$_2$ pressure of 100 to 400 bar wherein the amount of H$_2$ is 20 to 100 times the amount required stoichiometrically, over a pelletized catalyst which is free from Zn oxide and which is made up of pressed powders of Cu, Mn and Al oxides with at least one oxide of a metal of subgroup VI of the Periodic Table of the Elements (Mendeleev).

2. The process of claim 1 in which the oligoesterification is carried out in one esterification step with the removal of water of reaction by distillation, within the temperature range from 100 to 240° C. and within the pressure range from 100 to 1500 mbar.

3. The process of claim 1 in which the oligoester which is used is produced from a mixture of 1.0 to 1.15 moles diol per mole of dicarboxylic acid, so that an average degree of esterification of 4 is achieved.

4. The process of claim 1 in which the oligoester which is used is employed without further purification in the hydrogenation step.

5. The process of claim 1 in which the mixture of pressed oxide powders has a Cu content of 30.0 to 55.0% by weight, has a Mn content of 3.0 to 15.0% by weight, has an Al content of 10.0 to 25.0% by weight, and a subgroup VI oxide content of from 0.05 to 3.0% by weight, wherein the metal oxide content is calculated on the basis of the metal and is expressed with respect to the total amount of oxide powder mixture, and the balance constitutes oxygen up to 100% by weight.

6. The process of claim 1 in which one or more oxides of subgroup VI of the Periodic Table of the Elements are present in the pressed oxide powder and the total amount thereof amounts to 0.1 to 0.8% by weight of the total oxide powder.

7. The process of claim 1 in which the catalyst additionally has a content of 0.5 to 7.0% by weight of an alkaline earth compound, calculated as the metal and expressed with respect to the amount of the total oxide powder.

8. The process of claim 1 in which the pelletized catalyst comprising pressed oxide powders is of cylindrical or spherical shape with dimensions of 2 to 10 mm and has a crushing strength of from 50 to 200 N on the surface of the shaped body, and an internal specific surface of from 10 to 90 $m^2/g$.

9. The process of claim 1 in which the catalyst comprising pressed oxide powder is activated before hydrogenation by treatment with $H_2$ at 180 to 280° C., wherein a mixture of 10 to 15% by volume $H_2$ and 90 to 85% by volume of an inert gas is used at the start of the treatment and the proportion of inert gas is reduced to zero % by volume in the course of the treatment.

10. The process of claim 1 in which the catalytic hydrogenation of the oligoester is conducted at a temperature of from 190 to 240° C.

11. The process of claim 10 in which the catalytic hydrogenation of the oligoester is conducted at a pressure of from 150 to 300 bar.

12. The process of claim 1 in which the catalytic hydrogenation of the oligoester is conducted at a pressure of from about 150 to about 300 bar.

13. The process of claim 1 in which the oligoester is produced from a mixture of from 1.05 to 1.10 moles of diol per mole of dicarboxylic acid.

14. The process of claim 1 in which the pelletized catalyzed has dimensions of from 3 to 7 mm, a crushing strength of from 70 to 170 N on the surface of the shaped body, and an internal specific surface of from about 30 to about 80 $m^2/g$.

* * * * *